United States Patent [19]

Jain

[11] Patent Number: 4,672,041

[45] Date of Patent: Jun. 9, 1987

[54] METHOD AND STABLE DIAZO REAGENT FOR DETECTING BILIRUBIN

[75] Inventor: Chandra P. Jain, Placentia, Calif.

[73] Assignee: Beckman Instruments, Inc., Fullerton, Calif.

[21] Appl. No.: 755,959

[22] Filed: Jul. 17, 1985

Related U.S. Application Data

[63] Continuation of Ser. No. 704,907, Feb. 22, 1985, abandoned, which is a continuation of Ser. No. 341,960, Jan. 22, 1982, abandoned.

[51] Int. Cl.$^4$ ............................................. G01N 33/72
[52] U.S. Cl. ..................................... 436/97; 436/903; 534/559
[58] Field of Search ................... 436/97, 903; 534/559

[56] References Cited

U.S. PATENT DOCUMENTS

| | | | |
|---|---|---|---|
| 2,062,873 | 12/1936 | Flett | 260/141S X |
| 2,812,321 | 11/1957 | Eberhart et al. | 260/141 P |
| 2,827,449 | 3/1958 | Kesler | 260/141 P |
| 3,511,607 | 5/1970 | Green | 436/903 X |
| 4,030,885 | 6/1977 | Das | 436/903 X |
| 4,038,031 | 7/1977 | Lam | 436/903 X |
| 4,078,892 | 3/1978 | Steinbrink, Jr. | 436/97 |

Primary Examiner—David L. Lacey
Assistant Examiner—Robert J. Hill, Jr.
Attorney, Agent, or Firm—William H. May; Arnold Grant; Julie E. Abers

[57] ABSTRACT

An improved reagent combination of the type comprising a first solution comprising an aryl amine and an acid; and a second solution comprising a nitrite compound. The regent combination is characterized in that is further comprises a salt, wherein the salt is present in any preselected distribution in the solutions.

Also, an improved method for colorimetrically determining bilirubin in a sample comprising mixing an aliquot of the above first solution with an aliquot of the above second solution to form a stable diazo reagent; contacting a sample to be assayed with a total bilirubin accelerator buffer system to form a prereaction medium; contacting the prereaction medium with the stable diazo reagent; and measuring the color of the azobilirubin formed form the coupling reaction of the stable diazo reagent with the bilirubin present in said sample.

In addition, an improved method for producing a diazo reagent of the type comprising reacting an aryl amine with a nitrite compound in the presence of an acid. The method is characterized in that the reaction also takes place in the presence of a salt.

21 Claims, 1 Drawing Figure

METHOD AND STABLE DIAZO REAGENT FOR DETECTING BILIRUBIN

This is a continuation of application Ser. No. 704,907 filed on Feb. 22, 1985, now abandoned, which in turn is a continuation of application Ser. No. 341,960 filed on Jan. 22, 1982, now abandoned.

BACKGROUND OF THE INVENTION

1. Field of the Invention

This invention relates to a diazo reagent, a method for producing the diazo reagent, and a total bilirubin assay employing the diazo reagent.

2. Description of the Prior Art

For years, spectrophotometric methods have been employed for the measurement of total bilirubin in serum. In these methods, bilirubin is coupled with a diazotized compound, e.g., p-diazobenzene sulfonic acid (p-DBS) to form a colored azobilirubin. The color intensity of the azobilirubin thus formed is measured spectrophotometrically.

To form the diazo reagent, an aryl amine is diazotized with a nitrite containing compound in the presence of an acid. For example, p-aminobenzene sulfonic acid is diazotized with sodium nitrite in the presence of hydrochloric acid. The resulting diazo reagent, e.g., p-DBS, is stable for only a few hours (1–4). Efforts have been made to stabilize p-DBS solutions by adding aromatic sulfonic acid (5) or the making of fluoroborate derivatives (6). These efforts have resulted in making p-DBS stable for one day at room temperature and three days when stored at 2°–8° C.

When a mixture nitriloaromatic sulfonic acid (7) was utilized to stabilize p-DBS solution, the stability of p-DBS improved to two days at room temperature and three months at 2°–8° C.

Although these approaches have improved the stability of diazo reagents, the advances achieved thereby have nevertheless been modest. Accordingly, it would be very desirable to develop a diazo reagent having even more pronounced stability.

SUMMARY OF THE INVENTION

In accordance with the present invention, there is provided an improved reagent combination which is capable of forming a diazo reagent of improved stability. More particularly, the improved reagent combination of the instant invention is of the type comprising a first solution comprising an aryl amine and an acid, and a second solution comprising a nitrite compound. The improved reagent combination is characterized in that it further comprises a salt, wherein the salt is present in any preselected distribution in the solutions.

The instant invention also comprises an improved method for colorimetrically determining bilirubin in a sample. More particularly, the improved method of the instant invention is of the type which comprises mixing an aliquot of a first solution comprising an aryl amine and an acid with an aliquot of a second solution comprising a nitrite compound to form a diazo reagent; contacting a sample to be assayed with a total bilirubin accelerator buffer system to form a prereaction medium; contacting the prereaction medium with the diazo reagent; and measuring the color of the azobilirubin formed from the coupling reaction of the diazo reagent with the bilirubin present in the sample. The improved method of the instant invention is characterized in that a salt is present in any preselected distribution in the solutions.

In addition, the instant invention also comprises an improved method for producing a diazo reagent. More particularly, the improved method of the instant invention is of the type comprising reacting an aryl amine with a nitrite compound in the presence of an acid to form a diazo reagent. The improved method is characterized in that the reaction also takes place in the presence of a salt.

DESCRIPTION OF THE PREFERRED EMBODIMENT

Figure 1:
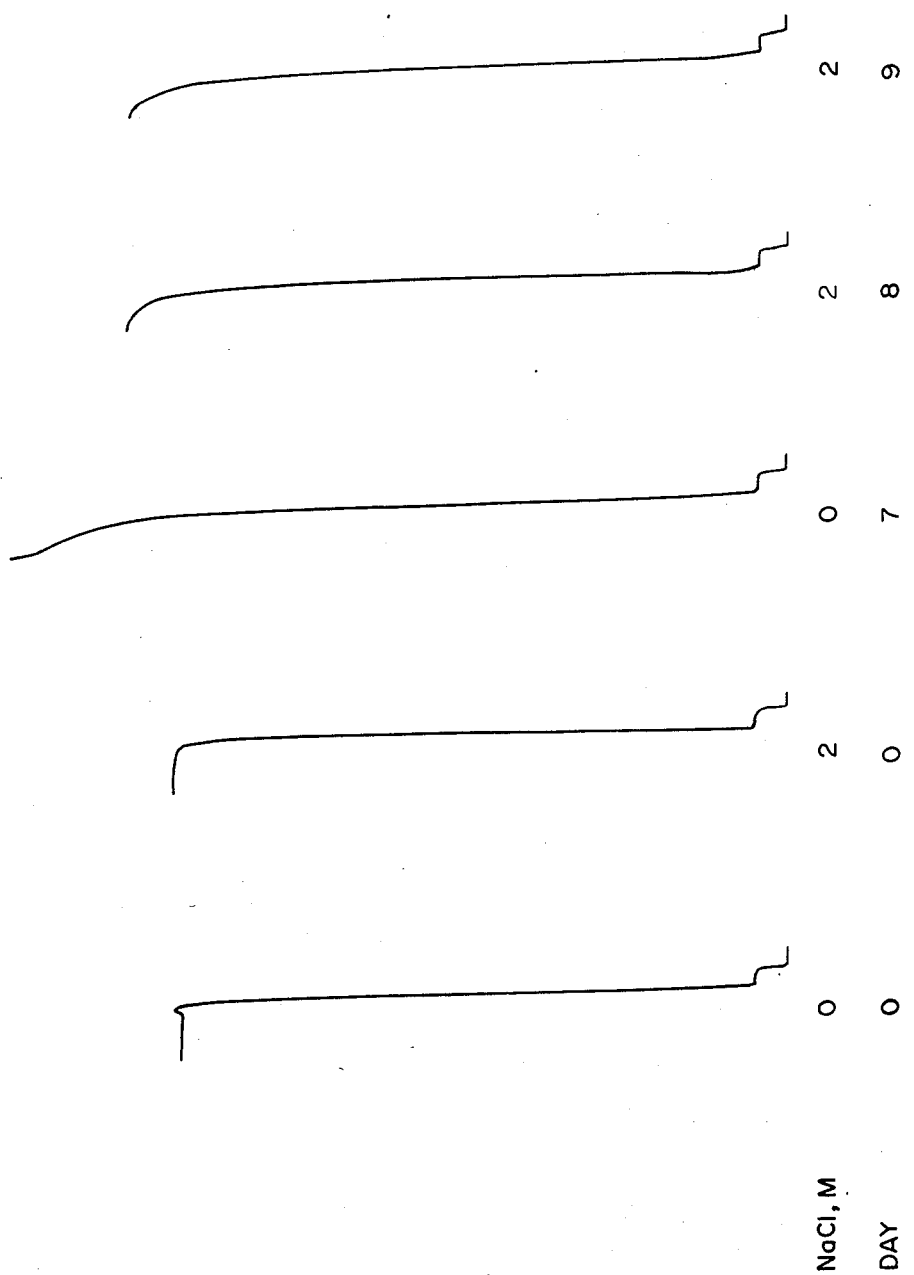
FIG. 1 depicts the results of the stability study of Example 3.

Virtually any aryl amine can be employed in the improved reagent combination of the instant invention. Typical aryl amines include, but are not limited to, 2,4-dichloroaniline, p-aminobenzene sulfonic acid, p-chloroaniline, 2-methoxy-5-nitroaniline, and p-toluidine. Preferably, the aryl amine is p-aminobenzene sulfonic acid.

The acid employed in the reagent combination of the instant invention has the formula $H_nX$ wherein X is selected from the group consisting of $Cl^-$ and $SO_4^{--}$, wherein n is the absolute value of the valence of X. Preferably, the acid is HCl.

The nitrite compound employed in the reagent combination of the instant invention has the formula $Y(NO_2)_m$, wherein Y is selected from a group consisting of $Na^+$, $K^+$, $Li^+$, and $Ca^{++}$, and m is the absolute value of the valence of Y. Preferably, the nitrite compound is $NaNO_2$.

The salt employed in the reagent of the instant invention has a formula $ZX_p$, wherein X is as defined above, Z is selected from a group consisting of $Na^+$, $K^+$, and $Li^+$, and p is the absolute value of the valence of Z. Preferably, the salt is NaCl.

Optionally, the reagent combination can also have ethylenediaminetetraacetic acid, tetrasodium salt (EDTA.Na4) present in the second solution.

In order to produce the stable diazo reagent of the instant invention, one reacts an aryl amine with a nitrite compound in the presence of an acid as well as in the presence of a salt. Accordingly, the reagent combination is formulated such that when one combines an aliquot of the first solution with an aliquot of the second solution to form a third solution, the molar ratio of the aryl amine and the acid to the nitrite moiety of the nitrite compound is such that at least one mole of aryl amine is present per mole of $NO_2^-$ and at least 2.5 moles of acid are present per mole of $NO_2^-$. Preferably, the first and second solutions are formulated such that the resulting third solution formed from preselected aliquots of the first and second solutions comprises from about 1.5 to about 8 moles of aryl amine per mole $NO_2^-$ and from about 4 to about 18 moles of acid per mole $NO_2^-$. More preferably, the molar ratio present in the third solution is about 3 moles of aryl amine per mole $NO_2^-$ and about 9 moles of acid per mole $NO_2^-$.

With respect to the amount of salt present, the improved reagent combination of the instant invention is formulated such that at least one of the first or second solutions comprises up to a saturating amount of salt. Preferably, at least one of the first or second solutions comprises from about 1M to about saturation, more preferably from about 1.5 to about 2.5 molar, salt. Optimally, at least one of the first and second solutions comprise about 2 molar salt. In addition, the salt is preferably present in at least the first solution.

The improved reagent combination of the instant invention can be employed in a colorimetric method to determine total bilirubin in a sample. In general, the colorimetric method entails mixing an aliquot of the first solution with an aliquot of the second solution to form the stable diazo reagent of this invention. The sample to be assayed is contacted with any total bilirubin accelerator system known to those skilled in the art, e.g., see Lolekha et al., Clin. Chem., 23(4):778 (1977), to form a prereaction medium. (The preferred total bilirubin accelerator system is of the type proposed by Jendrassik and Grof, Biochem. Z., 297:81 (1938) and comprises 0.39M sodium benzoate, 0.19M caffeine, and 0.69M sodium acetate.) The prereaction medium is contacted with the stable diazo reagent of this invention and the color of the azobilirubin formed from the coupling reaction of the diazo reagent with the bilirubin present in the sample is measured.

The following examples are provided for the purpose of further illustration only and are not intended to be limitations on the disclosed invention.

EXAMPLE 1

The following is the composition of a preferred reagent combination of the instant invention when a dilution factor of 100 parts first solution to 1 part second solution is employed:

| Ingredients | Optimal Conc., M | Preferred Conc. Range, M |
|---|---|---|
| First Solution | | |
| p-aminobenzene sulfonic acid | 0.03 | 0.015–0.08 |
| hydrochloric acid | 0.09 | 0.04–0.18 |
| sodium chloride | 2 | 1.5–2.5 |
| Second Solution | | |
| sodium nitrite | 1.1 | 1.1 |
| EDTA.Na4 | 0.0023 | 0–0.004 |

The preferred reagent, prepared in accordance with the parameters set forth in this example, will have a ZCl to amine molar ratio of about 18.75:1 (where 0.08M p-aminobenzene sulfonic acid and 1.5M sodium chloride are used) to about 166.7:1 (where 0.015M p-aminobenzene sulfonic acid and 2.5M sodium chloride are used).

EXAMPLE 2

Various reagent combinations wherein the first solution comprised 0.03 molar p-aminobenzene sulfonic acid and varying amounts of hydrochloric acid and sodium chloride as shown in Table I and wherein the second solution comprised 1.1 molar sodium nitrite and 2.3 millimolar EDTA.Na4 were mixed and allowed to stand at lab temperature. The stability of each of the resulting diazo reagents was evaluated by periodically measuring their absorbance. The results obtained from this study are set forth in Table I.

TABLE I[1]

| NaCl, M | HCl, M | Absorbance, 530 nm | |
|---|---|---|---|
| | | 5 days | 10 days |
| 0.0 | 0.09 | 1.229 | 1.640 |
| 0.1 | 0.09 | 1.137 | 1.612 |
| 0.5 | 0.09 | 0.993 | 1.347 |
| 1.0 | 0.09 | 0.617 | 0.934 |
| 2.0 | 0.09 | 0.355 | 0.380 |
| 0.0 | 0.18 | N/A[2] | 1.152 |
| 2.0 | 0.18 | 0.065 | 0.104 |

[1] All reagents comprised 0.030 M p-aminobenzene sulfonic acid; 10.0 mM sodium nitrite; and 0.023 mM EDTA.Na4.
[2] N/A denotes not available.

The data set forth in Table I indicate that diazo reagents formed from reagent combinations devoid of salt exhibit significant changes with respect to their colorimetric absorbance over time when compared with similar diazo reagents formulated from reagent combinations containing salt. As is well known to those skilled in the art, an increase in the absorbance of a diazo reagent is indicative of the degree of deterioration of the diazo salt present therein, i.e., the diazo salt, upon decomposition, forms various colored products. Accordingly, the data set forth in Table I indicate that diazo reagents formed from reagent combinations having varying amounts of salt present therein are more stable than corresponding diazo reagent formed from reagent combinations devoid of such salt.

EXAMPLE 3

Various reagent combinations wherein the first solution comprised 0.03 molar p-aminobenzene sulfonic acid, 0.09 molar HCl, and varying amounts of sodium chloride as shown in FIG. 1 and wherein the second solution comprised 1.0 molar sodium nitrite and 2.3 millimolar EDTA.Na4 were mixed and allowed to stand at lab temperature. The stability of each of the resulting diazo reagents was evaluated by periodically employing 0.1 ml of each diazo reagent and 1 ml of an accelerator buffer system to assay 35 μl of a sample containing 20 mg/dl bilirubin. The results obtained from this study are set forth in FIG. 1.

The reaction curves set forth in FIG. 1 indicate that a 7 day old diazo reagent formed from a reagent combination devoid of salt is incapable of achieving a steady state, i.e., is incapable of coupling with substantially all the bilirubin present in the assayed sample within the allotted reaction time (21 seconds). This fact is evidenced by the inability of the curve to achieve a substantially horizontal position within the allotted reaction time, thus indicating a decomposition of the diazo salt present in the diazo reagent. In contrast, similar, 8 and 9 day old diazo reagents formulated from a reagent combination containing salt were able to achieve steady states within the allotted reaction time. Accordingly, the curves of FIG. 1 indicate that diazo reagents formulated from a reagent combination having salt present therein are more stable than a corresponding diazo reagent formulated from a reagent combination devoid of such salt.

Based on this disclosure, many other modifications and ramifications will naturally suggest themselves to those skilled in the art. These are intended to be comprehended as within the scope of this invention.

Bibliography

1. U.S. Pat. No. 3,652,222,
2. U.S. Pat. No. 4,115,064,
3. Gilford—"Measurement of Total Bilirubin"

4. Technicon—"SMA II Reagents for the Measurement of Total Bilirubin",
5. Centrifichen—"measurement of Total Bilirubin",
6. Cal Biochem—"Pualey's Reagent",
7. Canadian Pat. No. 1,086,719.

The embodiments of the invention in which an exclusive property or privilege is claimed are defined as follows:

1. A reagent system comprising a first solution comprising an aryl amine and HCl and a second solution comprising a nitrite compound, wherein:
   (a) said reagent system further comprises a salt present in at least one of said solutions, said salt having a formula ZCl, wherein Z is selected from the group consisting of $Na^+$, $K^+$, and $Li^+$; and
   (b) said first and second solutions are formulated such that upon combining a predetermined aliquot of said first solution with a predetermined aliquot of said second solution a third solution results which has a ZCl to amine molar ratio of at least about 18.75:9 molar ratio of said aryl amine to the nitrite moiety of said nitrite compound of at least one mole of aryl amine per mole of $NO_2^-$ and a molar ratio of said HCl to the nitrite moiety of said nitrite compund of at least 2.5 moles of HCl per mole of $NO_2^-$.

2. The reagent system of claim 1 wherein said molar ratio of said aryl amine to the nitrite moiety of said nitrite compound is from about 1.5 to about 8 moles of aryl amine per mole of $NO_2^-$.

3. The reagent system of claim 1 wherein said molar ratio of said HCl to the nitrite moiety said nitrite compound is from about 4 to about 18 moles of HCl per mole of $NO_2^-$.

4. The reagent system of claim 1 wherein said molar ratio of said aryl amine to the nitrite moiety of said nitrite compound is from about 1.5 to about 8 moles of aryl amine per mole of $NO_2^-$ and said molar ratio of said HCl to the nitrite moiety of said nitrite compound is from about 4 to about 18 moles of HCl per mole of $NO_2^-$.

5. The reagent system of claim 1 wherein said salt is present in at least said first solution.

6. The reagent system of claim 1 wherein said ZCl to amine molar ratio is from about 18.75:1 to about 166.7:1.

7. The reagent system of claim 1 wherein Z is $Na^+$.

8. The reagent system of claim 1 wherein said ZCl to amine molar ratio is from about 18.75:1 to about 166.7:1 and Z is $Na^+$.

9. A reagent system comprising a first solution comprising an aryl amine and HCl and a second solution comprising a nitrite compound; wherein:
   (a) said reagent system further comprises a salt present in at least one of said solutions, said salt having a formula ZCl, wherein Z is selected from the group consisting of $Na^+$, $K^+$, and $Li^+$;
   (b) at least one of said first or second solutions comprises about 1M to saturation ZCl; and
   (c) said first and second solutions are formulated such that upon combining a predetermined aliquot of said first solution with a predetermined aliquot of said second solution, 9 third solution results which has a ZCl to amine molar ratio of at least about 18.75:9 molar ratio of said aryl amine to the nitrite moiety of said nitrite compound of least one mole of aryl amine per mole of $NO_2^-$ and a molar ratio of said HCl to the nitrite moiety of said nitrite compound of at least 2.5 moles of HCl per mole of $NO_2^-$.

10. The reagent system of claim 9 wherein said molar ratio of said aryl amine to the nitrite moiety of said nitrite compound is from about 1.5 to about 8 moles of aryl amine per mole of $NO_2^-$.

11. The reagent system of claim 9 wherein said molar ratio of said HCl to the nitrite moiety of said nitrite compound is from about 4 to about 18 moles of HCl per mole of $NO_2^-$.

12. The reagent system of claim 9 wherein said salt is present in at least said first solution.

13. The reagent system of claim 9 wherein said ZCl to amine molar ratio is from about 18.75:1 to about 166.7:1.

14. The reagent system of claim 9 wherein Z is $Na^+$.

15. The reagent system of claim 9 wherein said ZCl to amine molar ratio is from about 18.75:1 to about 166.7:1 and Z is $Na^+$.

16. The reagent system of claim 9 wherein said molar ratio of said aryl amine to the nitrite moiety of said nitrite compound is from about 1.5 to about 8 moles of aryl amine per mole of $NO_2^-$ and said molar ratio of said HCl to the nitrite moiety of said nitrite compound is from about 4 to about 18 moles of HCl per mole of $NO_2^-$.

17. The reagent system of claim 16 wherein said salt is present in at least said first solution.

18. The reagent system of claim 16 wherein said ZCl to amine molar ratio is from about 18.75:1 to about 166.7:1.

19. The reagent system of claim 16 wherein Z is $Na^+$.

20. The reagent system of claim 16 wherein said ZCl to amine molar ratio is from about 18.75:1 to about 166.7:1 and Z is $Na^+$.

21. A method for colorimetrically determining bilirubin in a sample comprising:
   (a) mixing a first aliquot of said first solution of any one of claims 1, 9, or 2-20 and a second aliquot of said second solution of any one of claims 1, 9 or 2-20, such that said first and second aliquots are taken from said first and second solutions of the same claim, in a ratio of about 100 parts first solution to about 1 part second solution to form a diazo reagent;
   (b) contacting a sample to be assayed with a total bilirubin accelerator buffer system to form a pre-reaction medium;
   (c) contacting said prereaction medium with said diazo reagent; and
   (d) measuring the color of any azobilirubin formed from a coupling reaction of said diazo reagent with any bilirubin present in said sample.

* * * * *